(12) United States Patent
Fisk et al.

(10) Patent No.: US 10,087,164 B2
(45) Date of Patent: Oct. 2, 2018

(54) SYNTHESIS OF 6-ARYL-4-AMINOPICOLINATES AND 2-ARYL-6-AMINOPYRIMIDINE-4-CARBOXYLATES BY DIRECT SUZUKI COUPLING

(71) Applicant: Dow AgroSciences LLC, Indianapolis, IN (US)

(72) Inventors: Jason S. Fisk, Freeland, MI (US); Xiaoyong Li, Midland, MI (US); Mark Muehlfeld, Midland, MI (US); Robert S. Bauman, Bay City, MI (US); Jossian Oppenheimer, Midland, MI (US); Siyu Tu, Midland, MI (US); Mark A. Nitz, Midland, MI (US); Reetam Chakrabarti, Collegeville, PA (US); Shawn D. Feist, Midland, MI (US); James W. Ringer, Midland, MI (US); Ronald B. Leng, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/599,716

(22) Filed: May 19, 2017

(65) Prior Publication Data
US 2017/0334878 A1 Nov. 23, 2017

Related U.S. Application Data

(60) Provisional application No. 62/416,811, filed on Nov. 3, 2016, provisional application No. 62/338,562, filed on May 19, 2016.

(51) Int. Cl.
*C07D 213/90* (2006.01)
*C07D 401/04* (2006.01)
*C07D 239/28* (2006.01)
*B01J 35/00* (2006.01)
*C07D 213/79* (2006.01)
*C07D 239/02* (2006.01)
*C07D 239/32* (2006.01)

(52) U.S. Cl.
CPC ........ *C07D 401/04* (2013.01); *B01J 35/0046* (2013.01); *C07D 213/79* (2013.01); *C07D 213/90* (2013.01); *C07D 239/02* (2013.01); *C07D 239/28* (2013.01); *C07D 239/32* (2013.01); *B01J 2231/4211* (2013.01)

(58) Field of Classification Search
None
See application file for complete search history.

(56) References Cited

U.S. PATENT DOCUMENTS

| | | | |
|---|---|---|---|
| 2012/0190549 A1* | 7/2012 | Eckelbarger | C07F 7/0812 504/193 |
| 2012/0190857 A1* | 7/2012 | Arndt | C07D 213/79 546/289 |
| 2013/0172566 A1* | 7/2013 | Oppenheimer | C07D 213/803 546/310 |

* cited by examiner

*Primary Examiner* — Zinna Northington Davis
(74) *Attorney, Agent, or Firm* — Nicholas M. Kunz

(57) ABSTRACT

Improved methods of synthesizing 6-aryl-4-aminopicolinates, such as arylalkyl and alkyl 4-amino-3-chloro-6-(4-chloro-2-fluoro-3-methoxyphenyl)pyridine-2-carboxylates and arylalkyl and alkyl 4-amino-3-chloro-5-fluoro-6-(4-chloro-2-fluoro-3-methoxyphenyl)pyridine-2-carboxylates, are described herein. The improved methods include a direct Suzuki coupling step, which eliminates the protection/deprotection steps in the current chemical process, and therefore eliminates or reduces various raw materials, equipment and cycle time as well as modification of other process conditions including use of crude AP, use of ABA-diMe, and varying pH, catalyst concentration, solvent composition, and/or workup procedures. This invention was expanded to include synthesis of 2-aryl-6-aminopyrimidine-4-carboxylates.

45 Claims, No Drawings

SYNTHESIS OF 6-ARYL-4-AMINOPICOLINATES AND 2-ARYL-6-AMINOPYRIMIDINE-4-CARBOXYLATES BY DIRECT SUZUKI COUPLING

This application claims a priority based on provisional applications 62/338,562 and 62/416,811, which were filed in the U.S. Patent and Trademark Office on May 19, 2016 and Nov. 3, 2016 respectfully. The entire disclosure of which is hereby incorporated by reference.

FIELD OF THE INVENTION

Improved methods of synthesis of 6-aryl-4-aminopicolinates and 2-aryl-4-aminopyrimidine-4-carboxylates, in which the number of reaction steps is reduced and various reaction conditions are modified from current literature procedures, are described herein.

BACKGROUND OF THE INVENTION 6-aryl-4-aminopicolinates, such as methyl 4-amino-3-chloro-6-(4-chloro-2-fluoro-3-methoxyphenyl)picolinate, and 6-aryl-4-amino-5-fluoropicolinates, such as benzyl 4-amino-3-chloro-5-fluoro-6-(4-chloro-2-fluoro-3-methoxyphenyl)picolinate, are high value herbicides recently developed and marketed by Dow AgroSciences LLC. The current syntheses for some 6-aryl-4-aminopicolinates and 6-aryl-4-amino-5-fluoropicolinates involve a multi-step process for coupling the head and tail portions of the molecules via Suzuki coupling. For the synthesis of 6-aryl-4-aminopicolinates, the process typically involves protection of a 4-amino-2-chloropicolinate, for example, acetylation of 4-amino-2-chloropicolinate, to enable a high yield Suzuki coupling with an arylboronic acid. Subsequent deprotection via deacetylation affords the final desired product. This process is represented by the current literature reaction scheme for methyl 4-amino-3-chloro-6-(4-chloro-2-fluoro-3-methoxyphenyl)pyridine-2-carboxylate shown in part in Scheme 1:

Scheme 1: Synthesis of methyl 4-amino-3-chloro-6-(4-chloro-2-fluoro-3-methoxyphenyl)picolinate.

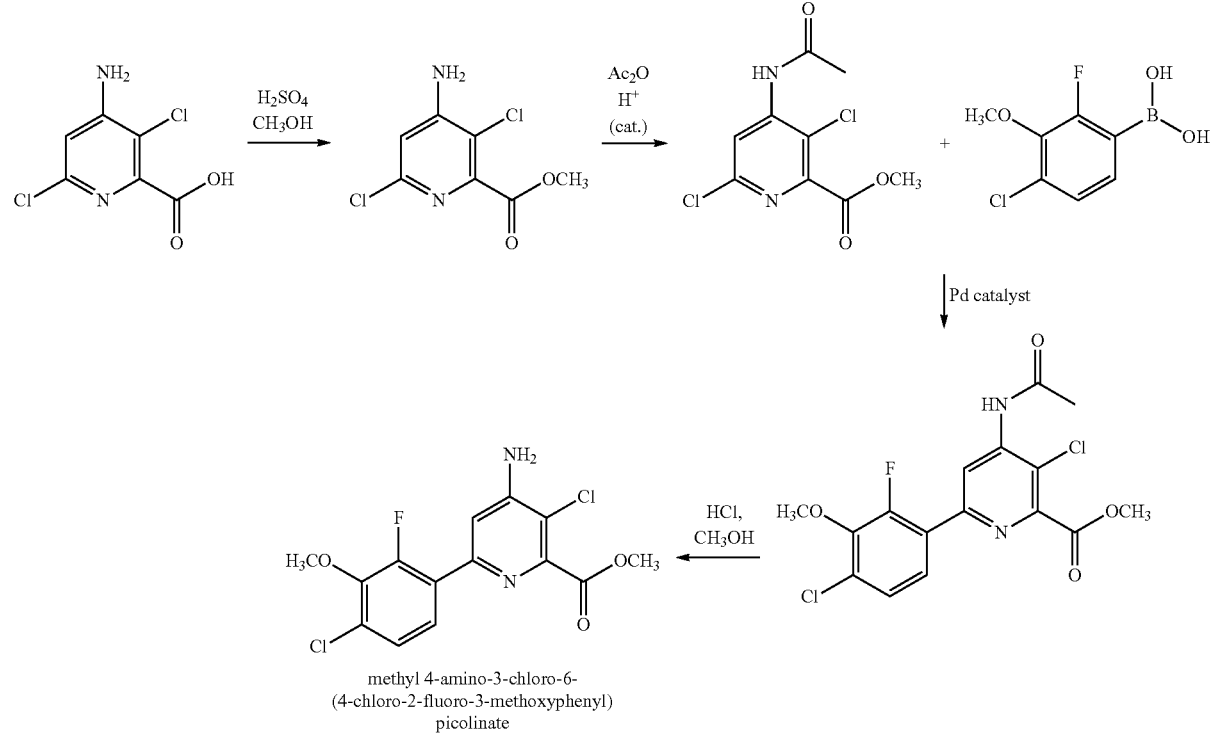

In addition, procedures that do not involve protecting the amine group have been used to prepare 6-aryl-4-aminopicolinates and 2-aryl-6-aminopyrimidine-4-carboxylates from 4-amino-6-chloropicolinates and 6-amino-2-chloropyrimidine-4-carboxylates, respectively, by the Suzuki coupling reactions shown in Scheme 2.

Scheme 2: Synthesis of 6-aryl-4-aminopicolinates and 2-aryl-6-aminopyrimidine-4-carboxylates.

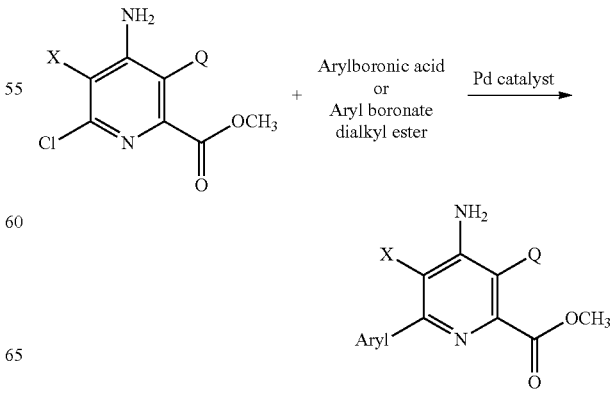

-continued

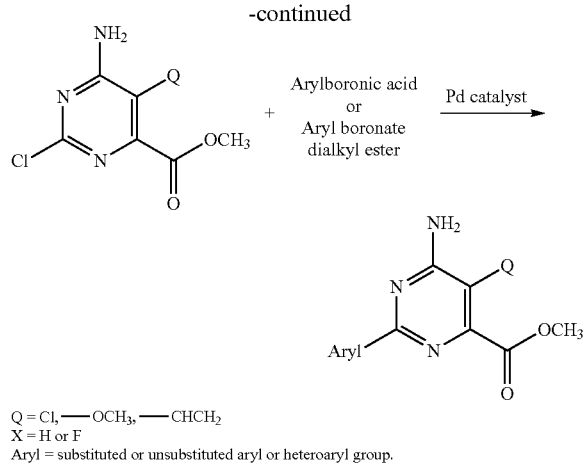

Q = Cl, —OCH₃, —CHCH₂
X = H or F
Aryl = substituted or unsubstituted aryl or heteroaryl group.

For the reaction sequence shown in Scheme 1, reducing the number of reaction steps would decrease the cost of synthesizing the compounds by eliminating or reducing raw materials, unit operations, equipment, and cycle time. For the reactions shown in Scheme 2, reducing the amount of palladium catalyst required for the Suzuki coupling step would also decrease the cost of synthesizing the compounds. For example, the current Suzuki coupling reaction conditions used to produce 6-aryl-4-aminopicolinates from 4-amino-6-chloropicolinates and 2-aryl-6-aminopyrimidine-4-carboxylates from 6-amino-2-chloropyrimidine-4-carboxylates require palladium catalyst loadings of 4% or higher to produce yields of desired coupled product greater than 60%. Considering the high cost of palladium and the fact that some palladium catalyst will inevitably be lost during the course of the Suzuki coupling reaction and catalyst recycling steps, improved Suzuki coupling reaction conditions that reduce the amount of required palladium catalyst loading to produce 6-aryl-4-aminopicolinates, 6-aryl-4-amino-5-fluoropicolinates, and 2-aryl-6-aminopyrimidine-4-carboxylates in high yield would significantly decrease the cost of producing these classes of molecules.

SUMMARY OF THE INVENTION

Improved methods of synthesis for 6-aryl-4-aminopicolinates, such as methyl 4-amino-3-chloro-6-(4-chloro-2-fluoro-3-methoxyphenyl)picolinate and benzyl 4-amino-3-chloro-5-fluoro-6-(4-chloro-2-fluoro-3-methoxyphenyl)picolinate, are described herein. Specifically, reaction conditions were identified to allow for the direct Suzuki coupling of an unprotected 4-amino-6-chloropicolinate, such as methyl 4-amino-3,6-dichloropicolinate and benzyl 4-amino-3,6-dichloro-5-fluoropicolinate, to afford 6-aryl-4-aminopicolinates, such as methyl 4-amino-3-chloro-6-(4-chloro-2-fluoro-3-methoxyphenyl)pyridine-2-carboxylates and benzyl 4-amino-3-chloro-5-fluoro-6-(4-chloro-2-fluoro-3-methoxyphenyl)pyridine-2-carboxylates in high yield (e.g., greater than 60%, 65%, 70%, 75%, 80%, or 85%) with palladium catalyst loadings less than 4%, for example from about 0.25% to about 3%, from about 0.25% to about 2.5%, from about 0.25% to about 2.0%, from about 0.25% to about 1.5%, from about 0.25% to about 1.0%, or from about 0.25% to about 0.5%. In some embodiments, the concentration of the palladium catalyst is about 0.5%.

Other improvements for the production of 6-aryl-4-aminopicolinates include: (1) the use of crude 4-amino-2-chloropicolinate without purification and/or isolation; (2) the use of dimethyl (4-chloro-2-fluoro-3-methoxyphenyl)boronate instead of (4-chloro-2-fluoro-3-methoxyphenyl)boronic acid; and (3) varying pH, catalyst concentration, solvent composition, and/or workup procedures.

Finally, reaction conditions were identified to allow for the direct Suzuki coupling of an unprotected 6-amino-2-chloropyrimidine-4-carboxylates to produce 2-aryl-6-aminopyrimidine-4-carboxylates, such as methyl 6-amino-5-chloro-2-(4-chloro-2-fluoro-3-methoxyphenyl)pyrimidine-4-carboxylate and methyl 6-amino-2-(4-chloro-2-fluoro-3-methoxyphenyl)-5-methoxypyrimidine-4-carboxylate in high yield (e.g., greater than 60%, 65%, 70%, 75%, 80%, or 85%) with palladium catalyst loadings less than about 4% or lower, such as less than about 3.5%, such as less than about 3%, less than about 2.5%, less than or equal to about 2%, less than or equal to about 1.5%, less than or equal to about 1%, or about 0.5%.

In some embodiments, the 6-aryl-4-aminopicolinate is one or more compounds of Formula I:

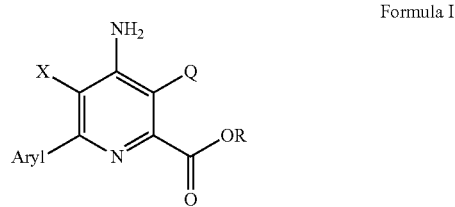

Formula I wherein

Q represents H, halogen (e.g., F or Cl), $C_1$-$C_3$ alkoxy, $C_1$-$C_3$ haloalkoxy, $C_2$-$C_4$ alkenyl, or $C_2$-$C_4$ haloalkenyl;

R represents H, alkyl (e.g, $C_{1-6}$ alkyl), aryl, or arylalkyl (e.g., benzyl);

X represents H; and

Aryl represents a substituted or unsubstituted aryl or heteroaryl group.

In some embodiments, the 6-aryl-4-aminopicolinate is one or more compounds of Formula II:

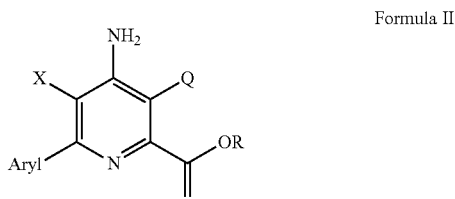

Formula II wherein

Q represents H, halogen (e.g., F or Cl), $C_1$-$C_3$ alkoxy, $C_1$-$C_3$ haloalkoxy, $C_2$-$C_4$ alkenyl, or $C_2$-$C_4$ haloalkenyl;

R represents H, alkyl (e.g, $C_{1-6}$ alkyl), or arylalkyl (e.g., benzyl);

X represents halogen (e.g., F or Cl), $C_{1-3}$ alkyl, $C_{1-3}$ alkoxy, or —$NO_2$; and Aryl represents a substituted or unsubstituted aryl or heteroaryl group.

In some embodiments, Aryl in Formula I and II is

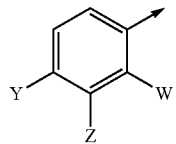

wherein
W represents H, F, Cl, $C_{1-3}$ alkyl, or $C_{1-3}$ alkoxy;
Y represents halogen, $C_{1-4}$ alkyl, $C_{1-4}$ haloalkyl, $C_{1-3}$ alkoxy, $C_{1-3}$ haloalkoxy, —CN, or —NO$_2$; and
Z represents H, F, Cl, $C_{1-4}$ alkyl, $C_{1-3}$ alkoxy, $C_1$-$C_4$ haloalkyl, $C_{1-3}$ haloalkoxy, $C_1$-$C_3$ alkoxy-substituted $C_1$-$C_3$ alkyl, or —NR$_1$R$_2$ wherein R$_1$ and R$_2$ are independently hydrogen, $C_1$-$C_3$ alkyl, or $C_1$-$C_3$ haloalkyl.

In some embodiments, Aryl in Formula I and II is

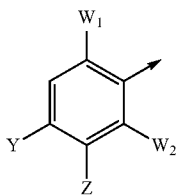

wherein
W$_1$ represents H or F;
W$_2$ represents H, F, Cl, $C_{1-3}$ alkyl, or $C_{1-3}$ alkoxy;
Y represents halogen, $C_{1-4}$ alkyl, $C_{1-4}$ haloalkyl, $C_{1-3}$ alkoxy, $C_{1-3}$ haloalkoxy, —CN, or —NO$_2$;
Z represents H, F, Cl, $C_{1-4}$ alkyl, $C_{1-3}$ alkoxy, $C_1$-$C_4$ haloalkyl, $C_{1-3}$ haloalkoxy, $C_1$-$C_3$ alkoxy-substituted $C_1$-$C_3$ alkyl, or —NR$_1$R$_2$, wherein R$_1$ and R$_2$ are independently hydrogen, $C_1$-$C_3$ alkyl, or $C_1$-$C_3$ haloalkyl; or
Y and Z or Z and W$_2$ taken together are a 5- or 6-membered aromatic or non-aromatic, carbocyclic or heterocyclic ring. Specific examples of this aryl can be found in International Application Nos. WO/2014/151005 and WO/2014/151009 which are incorporated herein by reference and include but are not limited to, the following examples A1-A36:

A1
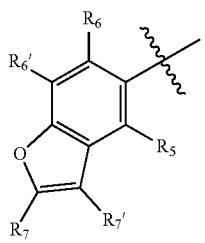

A2
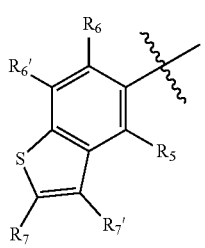

A3
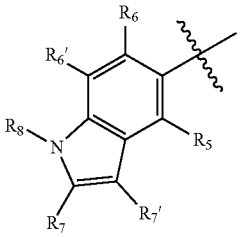

A4
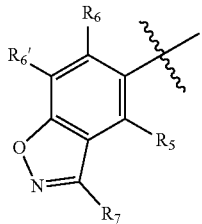

A5
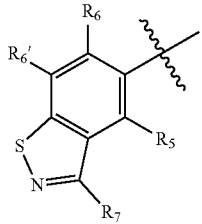

A6
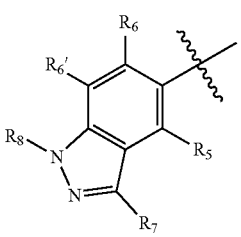

A7
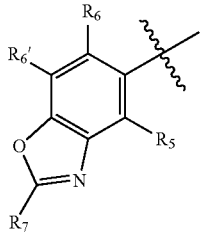

A8
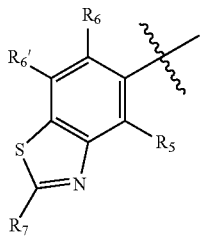

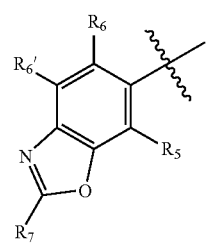 A9
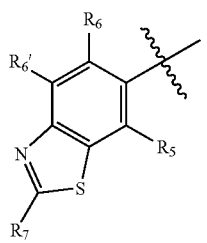 A10
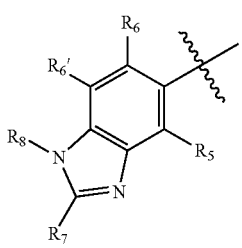 A11
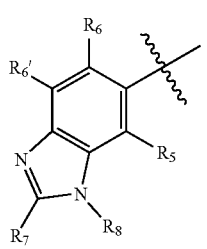 A12
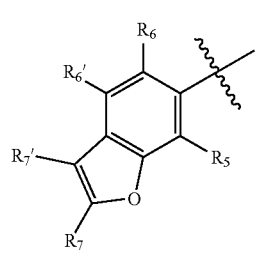 A13
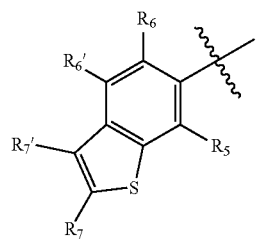 A14
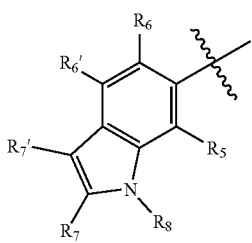 A15
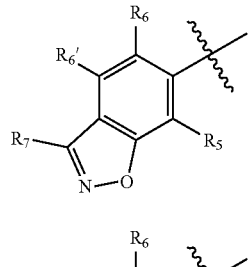 A16
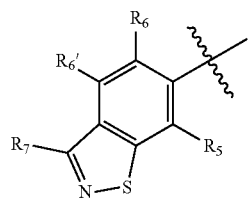 A17
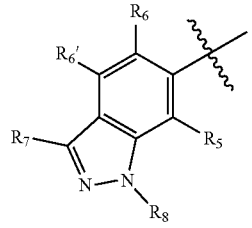 A18
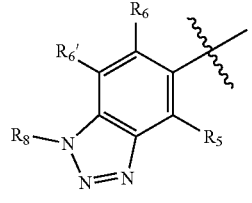 A19
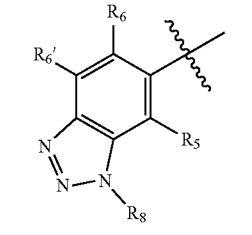 A20
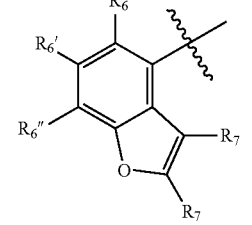 A21

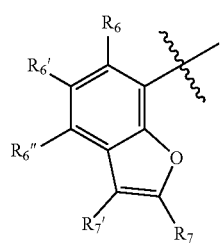 A22
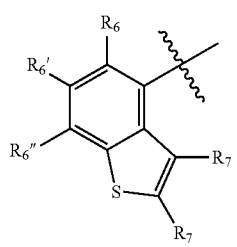 A23
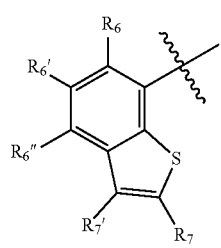 A24
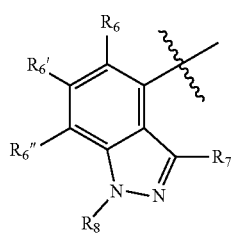 A25
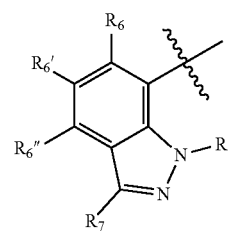 A26
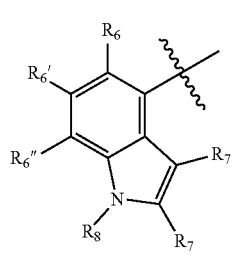 A27
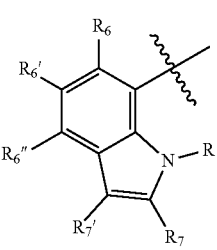 A28
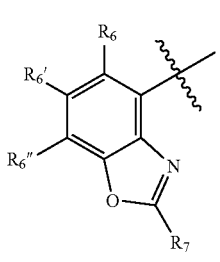 A29
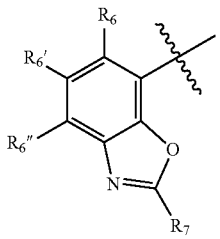 A30
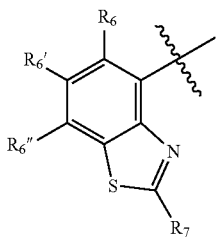 A31
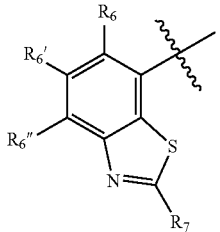 A32
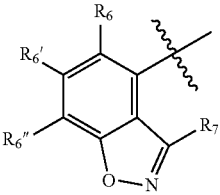 A33

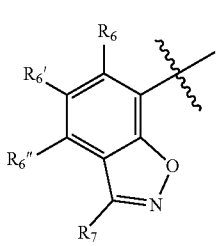

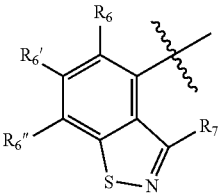

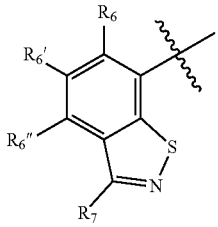

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$haloalkylamino, OH, CN, or $NO_2$;

$R^7$ and $R^7$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In still other embodiments, Aryl is defined as above wherein Y and Z or Z and $W_2$ are taken together to form a 5-membered non-aromatic heterocyclic ring. Specific examples of this Aryl can be found in International Application No. WO/2014/151008 which is incorporated herein by reference.

In some embodiments, the compound is a compound of Formula I, wherein the aryl group is 4-chloro-2-fluoro-3-methoxyphenyl or an ester thereof, such as the methyl ester. In other embodiments, the compound is a compound of Formula II, wherein X is fluorine and the aryl group is 4-chloro-2-fluoro-3-methoxyphenyl or an ester thereof, such as the benzyl ester. In still other embodiments, the compound is a compound of Formula II, where X is fluorine and the aryl group is a 7-fluoroindole or an ester thereof, such as the methyl ester.

In some embodiments, the 2-aryl-4-aminopyrimidine is one or more compounds of Formula III:

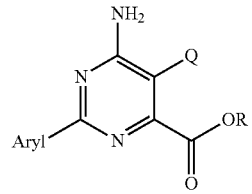

Formula III wherein

Q represents H, halogen (e.g., F or Cl), $C_1$-$C_3$ alkoxy, $C_1$-$C_3$ haloalkoxy, $C_2$-$C_4$ alkenyl, or $C_2$-$C_4$ haloalkenyl;

R represents H, alkyl (e.g, $C_{1-6}$ alkyl), or arylalkyl (e.g., benzyl); and

Aryl represents a substituted or unsubstituted aryl or heteroaryl group.

In some embodiments, Aryl in Formula III is

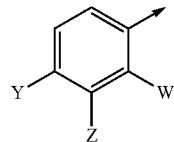

wherein

W represents H, F, Cl, $C_{1-3}$ alkyl, or $C_{1-3}$ alkoxy;

Y represents halogen, $C_{1-4}$ alkyl, $C_{1-4}$ haloalkyl, $C_{1-3}$ alkoxy, $C_{1-3}$ haloalkoxy, —CN, or —$NO_2$; and Z represents H, F, Cl, $C_{1-4}$ alkyl, $C_{1-3}$ alkoxy, $C_1$-$C_4$ haloalkyl, $C_{1-3}$ haloalkoxy, $C_1$-$C_3$ alkoxy-substituted $C_1$-$C_3$ alkyl, or —$NR_1R_2$, wherein $R_1$ and $R_2$ are independently hydrogen, $C_1$-$C_3$ alkyl, or $C_1$-$C_3$ haloalkyl.

In some embodiments, Aryl in Formula III is

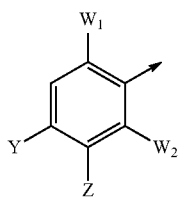

wherein $W_1$ represents H or F;

$W_2$ represents H, F, Cl, $C_{1-3}$ alkyl, or $C_{1-3}$ alkoxy;

Y represents halogen, $C_{1-4}$ alkyl, $C_{1-4}$ haloalkyl, $C_{1-3}$ alkoxy, $C_{1-3}$ haloalkoxy, —CN, or —$NO_2$;

Z represents H, F, Cl, $C_{1-4}$ alkyl, $C_{1-3}$ alkoxy, $C_1$-$C_4$ haloalkyl, $C_{1-3}$ haloalkoxy, $C_1$-$C_3$ alkoxy-substituted $C_1$-$C_3$ alkyl, or –$NR_1R_2$, wherein $R_1$ and $R_2$ are independently hydrogen, $C_1$-$C_3$ alkyl, or $C_1$-$C_3$ haloalkyl; or Y and Z or Z and $W_2$ taken together are a 5- or 6-membered aromatic or non-aromatic, carbocyclic or heterocyclic ring.

In still other embodiments, Aryl is defined as above wherein Y and Z or Z and $W_2$ are taken together to form a 5- or 6-membered aromatic or non-aromatic, carbocyclic or heterocyclic ring. Specific examples of this Aryl can be found in International Application Nos. WO/2014/151005 and WO/2014/151009 which are incorporated herein by reference and include but are not limited to the examples A1-A36 as defined above.

In still other embodiments, Aryl is defined as above wherein Y and Z or Z and $W_2$ are taken together to form a 5-membered non-aromatic heterocyclic ring. Specific examples of this Aryl can be found in International Application No. WO/2014/151008 which are incorporated herein by reference.

DETAILED DESCRIPTION OF THE INVENTION

Reaction conditions were identified to allow for the direct Suzuki coupling of an unprotected 4-amino-6-chloropicolinate, such as methyl 4-amino-3,6-dichloropicolinate and benzyl 4-amino-3,6-dichloro-5-fluoropicolinate, to afford 6-aryl-4-aminopicolinates, such as methyl 4-amino-3-chloro-6-(4-chloro-2-fluoro-3-methoxyphenyl)pyridine-2-carboxylate and benzyl 4-amino-3-chloro-5-fluoro-6-(4-chloro-2-fluoro-3-methoxyphenyl)pyridine-2-carboxylate in high yield (e.g., greater than 60%, 70%, 80%, or 90%). Other improvements for 6-aryl-4-aminopicolinates include use of the crude 4-amino-2-chloropicolinate without purification, use of dimethyl (4-chloro-2-fluoro-3-methoxyphenyl)boronate instead of (4-chloro-2-fluoro-3-methoxyphenyl)boronic acid, and varying pH, catalyst concentration, solvent composition, and/or workup procedures. Finally, reaction conditions were identified to allow for the direct Suzuki coupling of an unprotected 6-amino-2-chloropyrimidine-4-carboxylate to produce 2-aryl-6-aminopyrimidine-4-carboxylates, such as methyl 6-amino-5-chloro-2-(4-chloro-2-fluoro-3-methoxyphenyl)pyrimidine-4-carboxylate and methyl 6-amino-2-(4-chloro-2-fluoro-3-methoxyphenyl)-5-methoxypyrimidine-4-carboxylates, in high yield (e.g., greater than 60%, 65%, 70%, 75%, 80%, 85%, or 90%).

I. Definitions

"Aminopyridine" or "Aminopyrimidine" or "AP" as used herein refers to a substituted or unsubstituted 4-amino-6-chloropicolinate (or an ester thereof) or a 6-aminopyrimidine-4-carboxylic acid (or an ester thereof). "Substituted" as used herein in reference to the pyridine or pyrimidine, refers to one or more substituents on the pyridine or pyrimidine ring. Examples of suitable substituents include, but are not limited to, for example, hydroxy, nitro, cyano, formyl, halogen (e.g., Cl, Br, I, and F), $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl. In some embodiments, 4-aminopyridine-2-carboxylic acid or ester thereof is substituted at the 5-position with fluorine.

"Ester", as used herein, refers to the group —(C=O)OR, wherein R is alkyl, haloalkyl, alkenyl, alkynyl, or arylalkyl. In some embodiments, AP is used as the ester, such as the methyl ester or benzyl ester.

"Aryl boronic acid" or "ABA", as used herein, refers to a substituted or unsubstituted aromatic carbocyclic group, such as phenyl boronic acid ("PBA") or an heteroaryl boronic acid ("HBA"). "Substituted" as used herein, refers to one or more substituents on the phenyl or heteroaryl (e.g., 7-fluoroindole) ring. Examples of suitable substituents include, but are not limited to, hydroxy, nitro, cyano, formyl, halogen (e.g., Cl, Br, I, and F), $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl. In some embodiments, the ABA is 4-chloro-2-fluoro-3-methoxyphenylboronic acid or a (7-fluoro-1H-indol-6-yl)boronic acid.

"Aryl boronate dialkyl ester" or "ABA-diMe", as used herein, refers to a substituted or unsubstituted aromatic carbocyclic group, such as a phenyl boronate ester ("PBA-diMe") or an heteroaryl boronate ester ("HBA-diMe"). "Substituted" as used herein, refers to one or more substituents on the phenyl ring. Examples of suitable substituents include, but are not limited to, hydroxy, nitro, cyano, formyl, halogen (e.g., Cl, Br, I, and F), $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl. In some embodiments, the ABA-diMe is dimethyl (4-chloro-2-fluoro-3-methoxyphenyl)boronate or 7-fluoro-6-(4,4,5,5-tetramethyl-1,3,2-dioxaborolan-2-yl)-1-(triisopropylsilyl)-1H-indole.

As used herein, the term "alkyl" refers to saturated, straight-chained or branched saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include, but are not limited to, methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. Examples of suitable substituents include, but not limited to, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. In some embodiments, the substituents include cyano and $C_1$-$C_6$ alkoxy.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include, but not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$haloalkoxycarbonyl, $C_1$-$C_6$carbamoyl, $C_1$-$C_6$halocarbamoyl, hydroxycarbonyl, $C_1$-$C_6$alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. In some embodiments, the substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{ao}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include, but not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Alkenyl substituents may be unsubstituted or substituted with one or more chemical moieties. Examples of suitable substituents include, but are not limited to, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. In some embodiments, the substituents include cyano and $C_1$-$C_6$ alkoxy.

The term "haloalkenyl," as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include, but not limited to, $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, but are not limited to, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$haloalkylsulfonyl, $C_1$-$C_6$alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. In some embodiments, the substituents include cyano and $C_1$-$C_6$ alkoxy.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, but are not limited to, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. In some embodiments, the substituents include halogen, $C_1$-$C_2$ alkyl and $C_1$-$C_2$ haloalkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, alkoxy refers to a group of the formula R—O—, where R is alkyl as defined above. Unless otherwise specified, alkoxy groups wherein R is a $C_1$-$C_8$ alkyl group, $C_1$-$C_6$ group, $C_1$-$C_4$, or $C_1$-$C_3$ group are intended. Examples include, but are not limited to, methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include, but are not limited to, chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include, but are not limited to, methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methylpentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include, but are not limited to, chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

"Direct Suzuki coupling" or "Direct Coupling", as used herein, means reaction of an aminopyridine or aminopyrimidine (AP) and an arylboronic acid (ABA) or aryl boronate dialkyl ester (ABA-diMe) without protection and deprotection steps for the amine functional group, such as acetylation and deacetylation.

II. Direct Suzuki Coupling

The current literature processes for preparing 6-aryl-4-aminopicolinates and 2-aryl-6-aminopyrimidine-4-carboxylates, such as arylalkyl and alkyl 4-amino-3-chloro-6-(4-chloro-2-fluoro-3-methoxyphenyl)pyridine-2-carboxylates and arylalkyl and alkyl 4-amino-3-chloro-5-fluoro-6-(4-chloro-2-fluoro-3-methoxyphenyl)pyridine-2-carboxylates, are multiple step processes and include protection and deprotection steps. The procedure is shown in Scheme 1 above. The improved process described herein eliminates the protection and deprotection steps, thereby eliminating or reducing various raw materials, equipment needed and cycle time. Other improvements for the production of 6-aryl-4-aminopicolinates include: (1) the use of crude AP without purification and/or isolation; (2) the use of ABA-diMe instead of ABA; and (3) varying pH, catalyst concentration, solvent composition, and/or workup procedures. An example of the improved reaction scheme is shown below in Scheme 3:

Scheme 3: Improved procedure for synthesis of 6-aryl-4-aminopicolinates

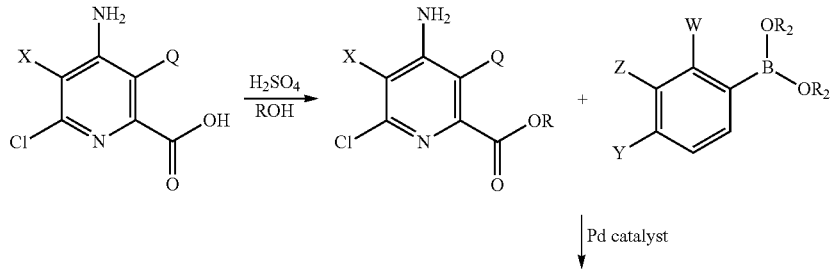

-continued

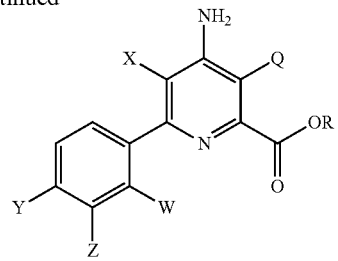

Q = H or Cl;
R = alkyl or arylalkyl;
R₂ = H, alkyl, or branched alkyl;
W = H, F, alkyl, or alkoxy;
X = H, F, or Cl;
Y = Cl; and
Z = alkoxy.

A. Use of Crude AP and/or ABA-diMe in the Direct Coupling

The current process to produce 6-aryl-4-aminopicolinates, such as methyl 4-amino-3-chloro-6-(4-chloro-2-fluoro-3-methoxyphenyl)pyridine-2-carboxylate, involves the palladium catalyzed Suzuki coupling reaction between isolated, protected AP and ABA, followed by deprotection of the coupled product. During the process of generating ABA, ABA-diMe is generated as an intermediate with the side product LiOMe, which needs to be neutralized prior to being charged to the subsequent coupling reaction. Since esterification of AP is catalyzed via sulfuric acid, it could serve as the acid to neutralize LiOMe. Accordingly, it was found that crude AP and crude ABA-diMe can be used directly in the direct coupling reaction with good yields under optimized conditions. Yields are typically greater than 50%, preferably greater than 55%, for example about 60% or greater, 65% or greater, 70% or greater, 75% or greater, 80% or greater, or 85% or greater.

B. pH of the Direct Coupling Reaction

The pH for the Suzuki coupling reaction can impact the yield of the reaction. Adjusting the pH for a given AP can significantly improve the yield of the reaction. In some embodiments, the pH is from about 7-12, preferably from about 7-10, more preferably from about 8-10. In some embodiments, the pH is from about 7 to about 8, from about 8 to about 9, or from about 9 to about 10. Adjusting the pH of the reaction mixture improved the overall yield of arylalkyl and alkyl 4-amino-3-chloro-6-(4-chloro-2-fluoro-3-methoxyphenyl)pyridine-2-carboxylates and arylalkyl and alkyl 4-amino-3-chloro-5-fluoro-6-(4-chloro-2-fluoro-3-methoxyphenyl)pyridine-2-carboxylates within the direct Suzuki coupling without impacting significantly the extent of the reaction. The pH can be adjusted using one or more bases. In some embodiments, the pH was adjusted using a mixture of potassium carbonate and potassium bicarbonate. In other embodiments, the pH was adjusted using only potassium carbonate or only potassium bicarbonate. The pH can also be adjusted using one or more bases in combination with carbon dioxide and water. Other inorganic bases such as the sodium carbonates (including bicarbonates), potassium acetate, sodium acetate, potassium phosphate bases (mono, di and tribasic), sodium tetraborate, potassium hydroxide, sodium hydroxide, cesium fluoride and potassium fluoride and organic bases such as triethylamine, triisopropylamine, diisopropylamine, diethylamine, and diisopropylethylamine can also be used. In another embodiment, the reaction mixture can be pretreated with carbon dioxide to adjust the pH prior to the Suzuki coupling reaction. Alternatively, the Suzuki coupling can be conducted in the presence of $CO_2$, e.g., bubbling $CO_2$ into the mixture reaction.

C. Catalyst Selection and Concentration

The Suzuki coupling reaction involves the use of a catalyst, including a ligand. Suitable catalysts include palladium catalysts, such as palladium (II) catalysts (e.g., palladium (II) acetate $Pd(OAc)_2$, palladium(II) chloride ($PdC_{12}$)), and $Pd(PPh_3)_4$; nickel catalysts, such as $NiCl_2$ (dppf) and $G_3DenP$-Ni; iron catalysts; copper catalysts; and ruthenium catalysts. The concentration of the catalyst can vary. In some embodiments, the concentration is less than 4%, preferably less than 3%, preferably about 2%. In some embodiments, the concentration of the catalyst is from about 0.2% to about 2.0% relative to the limiting reagent, preferably 0.4% to about 1.0%, more preferably about 0.5%. In some embodiments, the palladium catalyst is palladium (II) acetate. Suitable ligands for the catalyst system include, but are not limited to, trialkylphosphines and triarylphosphines. These include, but are not limited to, tri-tert-butylphosphine, Tricyclohexylphosphine, Di-tert-butylphenylphosphine, Dicyclohexylphenylphosphine, Triphenylphosphine, 4-Diphenylphosphinomethyl Polystyrene Resin crosslinked, Sodium Diphenylphosphinobenzene-3-sulfonate with 2% DVB, Tri(p-tolyl)phosphine, (±)-2,2'-Bis(diphenylphosphino)-1,1'-binaphthyl. The concentration of the ligand can vary. In some embodiments, the concentration of the ligand is from about 0.4% to about 8.0% relative to the limiting reagent, preferably 0.5% to about 6.0%, preferably 0.5% to about 4.0%, preferably 0.5% to about 2%, more preferably about 1.0%. In some embodiments, the ligand is triphenylphosphine ($PPh_3$).

D. Impact of Solvent on Direct Coupling

As discussed above, the Suzuki coupling reaction can be performed on crude AP without protection and deprotection steps. However, the reaction rate can be slow, even at an optimized pH, resulting in long reaction times. The AP direct coupling route was performed in a mixture of organic solvents containing methyl isobutyl ketone (MIBK), dimethoxyethane (DME), acetonitrile (MeCN), and methanol (MeOH). Improved direct coupling conditions were found to exist in systems that included a mixture of solvents such as MIBK, MeCN, MeOH, and water. Other solvent systems that can be effective in the direct coupling reaction using AP include ketones such as MIBK and/or alcohols such as benzyl alcohol and/or aromatic solvents such as toluene.

Another improvement to the solvent system is the elimination of water from the reaction mixture. The improved synthetic route includes performing the Suzuki coupling reaction between crude AP and ABA or crude ABA-diME under non-aqueous conditions. "Non-aqueous" as used in this context means that the base is added as a solid, not as an aqueous solution and no water is added to the reaction mixture to adjust the concentration. While the reaction solvents and/or reagents (e.g., AP-Me crude) are dried prior to use, residual water may remain. Such residual water may be present in "non-aqueous" systems. Exemplary non-aqueous solvent systems are demonstrated in Example 5.

EXAMPLES

Example 1. Direct Suzuki Coupling

Methyl 4-amino-3-chloro-6-(4-chloro-2-fluoro-3-methoxyphenyl)pyridine-2-carboxylate Methyl 4-amino-3,6-dichloropyridine-2-carboxylate (AP-Me) (8.00 g, 36.19 mmol), a 25.55 wt % solution of 4-chloro-2-fluoro-3-methoxy-phenylboronic acid (ABA) (33.30 g, 41.60 mmol), acetonitrile (23.9 mL) and water (28.0 mL) were added to a round bottom flask. The flask contents were sparged with nitrogen for 30 minutes as well as a 47 wt % aqueous solution of $K_2CO_3$ (26.6 g, 90.50 mmol, sparged separately). After loading the $K_2CO_3$ solution, triphenylphosphine (0.190 g, 0.724 mmol) and palladium acetate (0.081 g, 0.362 mmol) were added to the flask. The reaction was heated at 50° C. for 22 hours. After 22 h, the reaction was heated to 65° C. and the phase separated. The organic phase was analyzed to afford 81.4% yield of methyl 4-amino-3-chloro-6-(4-chloro-2-fluoro-3-methoxyphenyl)pyridine-2-carboxylate.

Methyl 4-amino-3-chloro-5-fluoro-6-(7-fluoro-1-(triisopropylsilyl)-1H-inden-6-yl)picolinate In a round bottom flask methyl 4-amino-3,6-dichloro-5-fluoropicolinate (AP) (0.5 g, 2.17 mmol), 7-fluoro-6-(4,4,5,5-tetramethyl-1,3,2-dioxaborolan-2-yl)-1-(triisopropylsilyl)-1H-indole (ABA-diMe) (1.1 g, 2.61 mmol), methanol (1.0 g, 31.0 mmol), 4-methyl-2-pentanone (1.2 g, 11.6 mmol), acetonitrile (1.3 g, 30.7 mmol), and water (1.9 g, 104.5 mmol) were combined. The mixture was sparged with nitrogen for 30 minutes before adding triphenylphosphine (0.02 g, 0.09 mmol) and palladium acetate (0.01 g, 0.04 mmol) in one portion. The reaction was heated to 50° C. and stirred for one hour at which time 47 wt % $K_2CO_3$ solution was added (0.13 g, 0.44 mmol). The reaction was stirred for another two hours at which time additional 47 wt % $K_2CO_3$ solution was added (0.15 g, 0.51 mmol). The reaction was stirred for another two hours at which time additional 47 wt % $K_2CO_3$ solution was added (0.29 g, 0.99 mmol). After 22 hr, the reaction was heated to 65° C. and then phase separated. The organic phase was analyzed to afford 72.1% yield of methyl 4-amino-3-chloro-5-fluoro-6-(7-fluoro-1-(triisopropylsilyl)-1H-inden-6-yl)picolinate.

Methyl 6-amino-5-chloro-2-(4-chloro-2-fluoro-3-methoxyphenyl)pyrimidine-4-carboxylate In a round bottom flask methyl 6-amino-2,5-dichloropyrimidine-4-carboxylate (AP) (3.0 g, 13.5 mmol), (4-chloro-2-fluoro-3-methoxyphenyl)boronic acid (ABA) (3.4 g, 16.2 mmol), methanol (3.0 g, 94.3 mmol), 4-methyl-2-pentanone (3.5 g, 35.2 mmol) and acetonitrile (7.8 g, 191.0 mmol) were combined. In a separate vial water (29.0 g) and potassium bicarbonate (3.4 g, 34.0 mmol) were combined to make a 10.5 wt % base solution. Both the reaction mixture and base solution were sparged with nitrogen for 30 minutes. To the reaction mixture was added base solution (13.8 g, 14.5 mmol), triphenylphosphine (0.14 g, 0.54 mmol), and palladium acetate (0.06 g, 0.27 mmol). The reaction was heated to 50° C. After 22 hr, the reaction was heated to 65° C. and then phase separated. The organic phase was analyzed to afford 68.1% yield of methyl 6-amino-5-chloro-2-(4-chloro-2-fluoro-3-methoxyphenyl)pyrimidine-4-carboxylate.

Methyl 6-amino-2-(4-chloro-2-fluoro-3-methoxyphenyl)-5-methoxypyrimidine-4-carboxylate In a round bottom flask methyl 6-amino-2-chloro-5-methoxypyrimidine-4-carboxylate (AP) (0.98 g, 4.7 mmol), (4-chloro-2-fluoro-3-methoxyphenyl)boronic acid (ABA) (1.0 g, 4.8 mmol), methanol (1.3 g, 40.6 mmol), 4-methyl-2-pentanone (1.1 g, 11.0 mmol) and acetonitrile (2.6 g, 63.3 mmol) were combined. In a separate vial water (9.7 g) and potassium bicarbonate (1.1 g, 11.0 mmol) were combined to make a 10.2 wt % base solution. Both the reaction mixture and base solutions were sparged with nitrogen for 30 minutes. To the reaction mixture was added base solution (5.2 g, 5.3 mmol), triphenylphosphine (0.05 g, 0.19 mmol), and palladium acetate (0.02 g, 0.09 mmol). The reaction was heated to 50° C. After 22 hr, the reaction was heated to 65° C. and then phase separated. The organic phase was analyzed to afford 75.6% yield of methyl 6-amino-2-(4-chloro-2-fluoro-3-methoxyphenyl)-5-methoxypyrimidine-4-carboxylate.

Benzyl 4-amino-3-chloro-6-(4-chloro-2-fluoro-3-methoxyphenyl)-5-fluoropicolinate In a round bottom flask benzyl 4-amino-3,6-dichloro-5-fluoropicolinate (AP) (1.5 g, 4.8 mmol), (4-chloro-2-fluoro-3-methoxyphenyl)boronic acid (ABA) (1.1 g, 5.3 mmol), methanol (1.0 g, 31.0 mmol), 4-methyl-2-pentanone (1.2 g, 11.6 mmol), acetonitrile (2.8 g, 68.2 mmol) and water (4.2 g) were combined. The mixture was sparged with nitrogen for 30 minutes before adding 47 wt % potassium carbonate (0.45 g, 1.5 mmol), triphenylphosphine (0.05 g, 0.19 mmol), and palladium acetate (0.02 g, 0.10 mmol). The reaction was heated to 60° C. and stirred for 30 minutes at which time 47 wt % $K_2CO_3$ solution was added (0.47 g, 1.6 mmol). The reaction was stirred for another 30 minutes at which time additional 47 wt % $K_2CO_3$ solution was added (0.10 g, 0.3 mmol). The reaction was stirred for another 30 minutes at which time additional 47 wt % $K_2CO_3$ solution was added (0.10 g, 0.3 mmol). After 2.5 hr, the reaction was heated to 65° C. and then phase separated. The organic phase was analyzed to afford 67.9% yield of benzyl 4-amino-3-chloro-6-(4-chloro-2-fluoro-3-methoxyphenyl)-5-fluoropicolinate.

Methyl 4-amino-3-chloro-6-(4-chloro-2-fluoro-3-methoxyphenyl)-5-fluoropicolinate In a round bottom flask methyl 4-amino-3,6-dichloro-5-fluoropicolinate (AP) (3.1 g, 13.0 mmol), (4-chloro-2- fluoro-3-methoxyphenyl)boronic acid (ABA) (3.0 g, 14.5 mmol), methanol (2.7 g, 84.3 mmol), 4-methyl-2-pentanone (3.1 g, 31.0 mmol), acetonitrile (7.6 g, 185.1 mmol) and water (11.3 g) were combined. The mixture was sparged with nitrogen for 30 minutes before adding 47 wt % potassium carbonate (1.2 g, 4.1 mmol), triphenylphosphine (0.07 g, 0.27 mmol) and palladium acetate (0.03 g, 0.13 mmol) in one portion. The reaction was heated to 60° C. and stirred for 30 minutes at which time 47 wt % $K_2CO_3$ solution was added (1.2 g, 4.1 mmol). The reaction was stirred for another 30 minutes at which time additional 47 wt % $K_2CO_3$ solution was added (0.8 g, 2.7 mmol). The reaction was stirred for another 30 minutes at which time additional 47 wt % $K_2CO_3$ solution was added (0.6 g, 2.0 mmol). After 5.5 hours, the reaction was heated to 65° C. and then phase separated. The organic phase was analyzed to afford 88.1% yield of methyl 4-amino-3-chloro-6-(4-chloro-2-fluoro-3-methoxyphenyl)-5-fluoropicolinate.

Example 2. Direct Coupling Using Crude AP and/or ABA-diMe

In a round bottom flask, 174.0 g of a crude methyl 4-amino-3,6-dichloropyridine-2-carboxylate (AP-Me) solution (which corresponds to 38.5 g, 174 mmol of AP-Me) was distilled under reduced pressure to a slurry. The slurry was transferred to a jacketed 1 L reactor and rinsed with an acetonitrile (112.0 g, 2728 mmol) rinse. $^1$HNMR analysis of the mixture indicated 574.2 of the desired 1037 mmol of methanol. Methanol (15.1 g, 471.3 mmol), water (189.0 g) and $K_2CO_3$ solution (47 wt %, 11.6 g, 39.4 mmol) was added to achieve a neutral pH, then 4-chloro-2-fluoro-3-methoxyphenylboronic acid (ABA) (36.9 g, 178.4 mmol) was added (1.01 molar equivalents of ABA was confirmed by HPLC) as well as 4-methyl-2-pentanone (38.7 g, 386.4 mmol). The mixture was sparged with nitrogen for 45 minutes before adding additional 47 wt % $K_2CO_3$ solution (16.0 g, 54.4 mmol), triphenylphosphine (0.46 g, 1.8 mmol), and palladium acetate (0.20 g, 0.9 mmol). The reaction was heated to 60° C. Additional 47 wt % $K_2CO_3$ solution was added at 30 minutes (16.0 g, 54.4 mmol), 60 minutes (12.2 g, 41.5 mmol), and 90 minutes (9.0 g, 30.6 mmol) after reaching 60° C. After 19 hr, the reaction was heated to 65° C. and phase separated. The organic phase was analyzed to afford 80.3% yield of methyl 4-amino-3-chloro-6-(4-chloro-2-fluoro-3-methoxyphenyl)pyridine-2-carboxylate.

In a jacketed reactor, 179.8 g of a crude methyl 4-amino-3,6-dichloropyridine-2-carboxylate (AP-Me) solution (which corresponds to 40.5 g, 183.2 mmol of AP-Me) was added, followed by 4-methyl-2-pentanone (225 g, 2250 mmol) and 12 wt % potassium bicarbonate (54.6 g, 65.4 mmol) to achieve a neutral pH. Brine solution was added to the neutralized solution then phase separated. The organic phase was distilled under reduced pressure to 30.6 wt % AP-Me. Acetonitrile (118.3 g, 2882 mmol), methanol (18.5 g, 577 mmol), and 4-chloro-2-fluoro-3-methoxy-phenylboronic acid (ABA) (41.1 g, 201.1 mmol) were added and the mixture was sparged with nitrogen for 45 minutes. To the reactor was added a solution of degassed 23 wt % potassium bicarbonate (45.1 g, 540 mmol), triphenylphosphine (0.47 g, 1.8 mmol), and palladium acetate (0.20 g, 0.9 mmol). The reaction was heated to 50° C. After 21 hours, the reaction was heated to 65° C. and then phase separated. The organic phase was analyzed to afford 94.6% yield of methyl 4-amino-3-chloro-6-(4-chloro-2-fluoro-3-methoxyphenyl) pyridine-2-carboxylate.

To a crude feed of AP-Me solution (41.4 g, which corresponds to 8.8 g, 40 mmol of AP-Me) was added 1.7 g sulfuric acid (98%). To the mixture feed, 73.4 g ABA-diMe solution (assayed 13.4 wt % ABA) was added slowly. The solvent was removed using a rotavap until the residual weight was around 55 g. To the oily mixture, 26.2 g MeCN, 10 g MIBK, and 44 g water were added. To the mixture, 15.8 g 47 wt % potassium carbonate was added. The slurry was sparged with nitrogen for 20 min, followed by the addition of 3.6 g 47 wt % potassium carbonate, palladium acetate (45 mg), and triphenylphosphine (105 mg). The reaction mixture was heated to 55° C. One hour and two hours after the mixture reached 55° C., another two shots of 3.6 g 47 wt % potassium carbonate solution were added. The mixture was reacted at 55° C. for additional 12 hr before filtration to remove solids. The in-process yield for methyl 4-amino-3-chloro-6-(4-chloro-2-fluoro-3-methoxyphenyl)pyridine-2-carboxylate was 60%.

Example 3. Direct Coupling as a Function of pH

Methyl 4-amino-3,6-dichloropyridine-2-carboxylate (AP-Me) (8.00 g, 36.19 mmol), a 25.55 wt % solution of 4-chloro-2-fluoro-3-methoxy-phenylboronic acid (ABA) (33.30 g, 41.60 mmol), acetonitrile (23.9 mL) and water (28.0 mL) were added to a round bottom flask. The flask contents were sparged with nitrogen for 30 minutes as well as a 47 wt % aqueous solution of $K_2CO_3$ (26.6 g, 90.50 mmol, sparged separately). After loading the $K_2CO_3$ solution (mixture pH-11.5), triphenylphosphine (0.190 g, 0.724 mmol) and palladium acetate (0.081 g, 0.362 mmol) were added to the flask. The reaction was heated at 50° C. for 22 hr. After 22 hr, the reaction was heated to 65° C. and the phase separated. The organic phase was analyzed to afford 81.4% yield of methyl 4-amino-3-chloro-6-(4-chloro-2-fluoro-3-methoxyphenyl)pyridine-2-carboxylate.

4-chloro-2-fluoro-3-methoxy-phenylboronic acid (ABA) solution (32.0 g), methyl 4-amino-3,6-dichloropyridine-2-carboxylale (AP-Me) (7.50 g, 95.99% pure, 33.9 mmol), and acetonitrile (29.3 mL, 23.0 g) were added to a round bottom flask. The resulting solution was orange-red in color. A solution of $K_2CO_3$ (3.91 g) and $KHCO_3$ (5.66 g) in water (40.1 mL) was prepared in a 100 mL bottle. Both the reactor and the aqueous base bottle were sparged with nitrogen for 30 min. The $K_2CO_3$—$KHCO_3$ solution was then transferred into the reactor via syringe (mixture pH-9), followed by addition of triphenylphosphine (0.178 g, 0.02 eq.) and palladium acetate (0.076 g, 0.01 eq.) in one portion. The mixture was stirred at 50° C. overnight and monitored by GC as well as LC. The reaction was stopped after 18 hr. After phase separation of the hot solution the organic phase was analyzed to afford 90.8% in process yield of methyl 4-amino-3-chloro-6-(4-chloro-2-fluoro-3-methoxyphenyl) pyridine-2-carboxylate.

Crude methyl 4-amino-3,6-dichloropyridine-2-carboxylate (AP-Me) solution (348.0 g, which corresponds to 75.9 g, 343.3 mmol of AP-Me) was distilled under reduced pressure to a slurry. Acetonitrile (225.5 g, 5493 mmol), water (347.4 g), and $K_2CO_3$ solution (47 wt %, 21.9 g, 74.5 mmol) were added to achieve a neutral pH, then 4-chloro-2-fluoro-3-methoxy-phenylboronic acid (ABA) (79.4 g, 383.8 mmol) and MIBK (83.4 g) were added. The mixture was sparged with nitrogen for 45 minutes before adding additional 47 wt % $K_2CO_3$ solution (30.5 g, 103.7 mmol), triphenylphosphine (1.35 g, 5.1 mmol), and palladium acetate (0.58 g, 2.6 mmol). The reaction was heated to 55° C. Additional 47 wt % $K_2CO_3$ solution (30.5 g, 103.7 mmol)

was added (mixture pH-7-8) one hour after reaching 55° C. and then again two hours after reaching 55° C. (30.5 g, 103.7 mmol). After 21 hr the reaction was heated to 65° C. and then phase separated. The organic phase was analyzed to afford 74.9% yield of methyl 4-amino-3-chloro-6-(4-chloro-2-fluoro-3-methoxyphenyl)pyridine-2-carboxylate.

A crude AP-Me feed (which contained 8.8 g, 40 mmol of AP-Me) was neutralized and extracted with methylisobutylketone (MIBK). The solvents were partially removed via rotavapor and the residual was redissolved with acetonitrile (26.2 g, 16 eq.) and MIBK (9.9 g, 2.46 eq.). ABA (9.4 g. 1.15 eq.), methanol (4.2 g, 3.3 eq.), and water (19.5 g, to dilute KF to 23 wt %) were added to the reaction flask. The mixture was sparged with nitrogen for 30 min, followed by the addition of KF (5.8 g, 2.5 eq.), palladium acetate (45 mg) and triphenylphosphine (105 mg). The reaction mixture was then heated to 50° C. and monitored using LC. The reaction was stopped after 24 hr, resulting in 69.8% in-process yield of methyl 4-amino-3-chloro-6-(4-chloro-2-fluoro-3-methoxyphenyl)pyridine-2-carboxylate.

A crude AP-Me feed (which contained 2.2 g, 10 mmol of AP-Me) was neutralized and extracted with MIBK. The solvents were partially removed via rotavapor and the residual was redissolved with MeCN (6.6 g, 16 eq.) and MIBK (5.9 g, 2.46 eq.). ABA (2.35 g. 1.15 eq.), MeOH (1 g, 3.3 eq.), and water (7.8 g, to dilute 47 wt % $K_2CO_3$ to 12 wt %) were added to the reaction flask. The mixture was sparged with nitrogen for 30 min, followed by the addition of 47% $K_2CO_3$ (0.88 g, 0.302 eq.), palladium acetate (11 mg), and triphenylphosphine (26 mg). The reaction mixture was then heated to 50° C. and held at that temperature. After the reaction temperature reached 50° C., a second portion of 47% $K_2CO_3$ (0.88 g) and a third portion were added via syringe after 1 hr and 2 hr, respectively. The reaction was stopped after 9 hr with the in-process yield of 88.3% of methyl 4-amino-3-chloro-6-(4-chloro-2-fluoro-3-methoxyphenyl)pyridine-2-carboxylate.

A crude AP-Me feed (which contained 2.2 g, 10 mmol of AP-Me) was neutralized and extracted with MIBK. The solvents were partially removed via rotavapor and the residual was redissolved with MeCN (6.6 g, 16 eq.) and MIBK (5.9 g, 2.46 eq.). ABA (2.35 g, 1.15 eq.), MeOH (1 g, 3.3 eq.) and water (7.8 g, to dilute 47 wt % $K_2CO_3$ to 12 wt %) were added to the reaction flask. The mixture was sparged with nitrogen for 30 min, followed by the addition of 47% $K_2CO_3$ (0.88 g, 0.302 eq.), palladium acetate (11 mg), and triphenylphosphine (26 mg). The reaction mixture was then heated to 50° C. and held at that temperature. After the reaction temperature reached 50° C., a second portion of 47% $K_2CO_3$ (0.88 g) and a third portion were added via syringe after 1 hr and 2 hr, respectively. An additional 0.2 g 47% $K_2CO_3$ was added 4 hr after reaching 50° C. The reaction was monitored via LC. The reaction was stopped after 8.5 hours which resulted in process yield of 89.7% of methyl 4-amino-3-chloro-6-(4-chloro-2-fluoro-3-methoxyphenyl)pyridine-2-carboxylate.

Methyl 4-amino-3,6-dichloropyridine-2-carboxylate (AP-Me) (8.00 g, 36.2 mmol), 4-chloro-2-fluoro-3-methoxyphenylboronic acid (ABA) (8.6 g, 41.6 mmol), acetonitrile (23.8 g), MIBK (8.6 g), methanol (3.7 g), aqueous $K_2CO_3$ solution (47 wt %, 11.2 g, 38.1 mmol), and water (11.5 g) were added to a round bottom flask. The pH of the mixture was ~10.5. The flask contents were sparged with carbon dioxide ($CO_2$) until the solution reached a steady-state pH of 8.6. Then triphenylphosphine (0.1 g, 0.36 mmol) and palladium acetate (0.04 g, 0.18 mmol) were added to the flask. The reaction was heated at 55° C. for 24 hours. After 24 hr, the reaction was heated to 65° C. and the phases separated. The organic phase was analyzed to afford 86.4% yield of methyl 4-amino-3-chloro-6-(4-chloro-2-fluoro-3-methoxyphenyl)pyridine-2-carboxylate.

Example 4. Direct Coupling Catalyst 4-chloro-2-fluoro-3-methoxy-phenylboronic acid (ABA) solution (32.0 g), methyl 4-amino-3,6-dichloropyridine-2-carboxylate (AP-Me) (7.50 g, 95.99% pure, 33.9 mmol), and acetonitrile (29.3 mL, 23.0 g) were added to a round bottom flask. A solution of $K_2CO_3$ (3.91 g) and $KHCO_3$ (5.66 g) in water (40.1 mL) was prepared in a 100 mL bottle. Both the reactor and the aqueous base bottle were sparged with nitrogen for 30 min. The $K_2CO_3$—$KHCO_3$ solution was then transferred into the reactor via syringe, followed by addition of triphenylphosphine (0.178 g, 0.02 eq.) and palladium acetate (0.076 g, 0.01 eq.) in one portion. The mixture was stirred at 50° C. overnight. The reaction was stopped after 18 hr. After phase separation of the hot solution the organic phase was analyzed to afford 90.8% in process yield of methyl 4-amino-3-chloro-6-(4-chloro-2-fluoro-3-methoxyphenyl)pyridine-2-carboxylate.

Crude methyl 4-amino-3,6-dichloropyridine-2-carboxylate (AP-Me) solution (348.0 g, (which corresponds to 75.9 g, 343.3 mmol of AP-Me) was distilled under reduced pressure to a slurry. Acetonitrile (225.5 g, 5493 mmol), water (347.4 g), and aqueous $K_2CO_3$ solution (47 wt %, 21.9 g, 74.5 mmol) were added to achieve a neutral pH, then 4-chloro-2-fluoro-3-methoxy-phenylboronic acid (ABA) (79.4 g, 383.8 mmol) and MIBK (83.4 g) were added. The mixture was sparged with nitrogen for 45 minutes before adding additional 47 wt % $K_2CO_3$ solution (30.5 g, 103.7 mmol), triphenylphosphine (1.35 g, 5.1 mmol), and palladium acetate (0.58 g, 2.6 mmol). The reaction was heated to 55° C. Additional 47 wt % $K_2CO_3$ solution (30.5 g, 103.7 mmol) was added one hour after reaching 55° C. and then again two hours after reaching 55° C. (30.5 g, 103.7 mmol). After 21 hr the reaction was heated to 65° C. and then phase separated. The organic phase was analyzed to afford 74.9% yield of methyl 4-amino-3-chloro-6-(4-chloro-2-fluoro-3-methoxyphenyl)pyridine-2-carboxylate.

A crude AP-Me feed (41.4 g, which corresponds to 8.8 g, 40.0 mmol of AP-Me) was distilled under reduced pressure to remove ~⅔ of the methanol until the residual weight reached 20.5 g. A thick slurry was retained and redissolved with 26.2 g acetonitrile. ABA (9.4 g, 1.15 eq.), MIBK (9.8 g), and water (40.4 g) were added to the AP-Me solution. 3.37 g 47 wt % $K_2CO_3$ solution was added, and the resulting mixture was sparged with nitrogen for 30 min. After sparging, 3.56 g 47% $K_2CO_3$ was added to the mixture, followed by palladium acetate (47 mg) and triphenylphosphine (105 mg) in one portion. The reaction mixture was then heated to 55° C. and held at that temperature. After the reaction temperature reached 55° C. two additional portions of 47% $K_2CO_3$ (3.56 g) were added via syringe after 1 hr and 2 hr, respectively. Four hours after the reaction temperature reached 55° C., another addition of 47% $K_2CO_3$ (3.56 g) occurred via syringe. The reaction was stopped after 9 hr, with an in process yield of 90.4% of methyl 4-amino-3-chloro-6-(4-chloro-2-fluoro-3-methoxyphenyl)pyridine-2-carboxylate In a round bottom flask crude methyl 4-amino-3,6-dichloropyridine-2-carboxylate (AP-Me) solution (348.0 g, which corresponds to 77.2 g, 349.0 mmol of AP-Me) was distilled under reduced pressure to a slurry. The slurry was transferred to a jacketed 1 L reactor and rinsed with an acetonitrile (224.0 g, 5456 mmol) rinse. ¹HNMR analysis of the mixture indicated 1047 of the desired 1117 mmol of methanol. Methanol (2.2 g, 68.7 mmol), water (378.0 g) and K$_2$CO$_3$ solution (47 wt %, 23.5 g, 79.9 mmol) were added to achieve a neutral pH, then 4-chloro-2-fluoro-3-methoxyphenylboronic acid (ABA) (78.7 g, 380.4 mmol) and 4-methyl-2-pentanone (82.7 g, 825.7 mmol) were added. The mixture was sparged with nitrogen for 45 minutes before adding additional 47 wt % K$_2$CO$_3$ solution (31.9 g, 108.5 mmol), triphenylphosphine (0.46 g, 1.8 mmol), and palladium acetate (0.20 g, 0.9 mmol). The reaction was heated to 60° C. Additional 47 wt % K$_2$CO$_3$ solution was added at 60 minutes (31.9 g, 108.5 mmol), 120 minutes (24.5 g, 83.3 mmol), and 240 minutes (18.1 g, 61.6 mmol) after reaching 60° C. After 20 hr, the reaction was heated to 65° C. and then phase separated. The organic phase was analyzed to afford 79.4% yield of methyl 4-amino-3-chloro-6-(4-chloro-2-fluoro-3-methoxyphenyl)pyridine-2-carboxylate.

Example 5. Impact of Solvent on Direct Coupling

A crude AP-Me feed (41.4 g, which corresponds to 8.8 g, 40.0 mmol of AP-Me) was distilled to remove ~⅔ of methanol until the residual weight reached 20.5 g. A thick slurry was retained and redissolved with 26.2 g MeCN (16 eq.). ABA (9.4 g, 1.15 eq.), MIBK (9.8 g), MeOH (4.3 g), and water (40.4 g) were added to the AP-Me solution. 3.2 g of 47 wt % K$_2$CO$_3$ solution was added, and the resulting mixture was sparged with nitrogen for 30 min. After sparging, 3.56 g 47% K$_2$CO$_3$ was added to the mixture, followed by palladium acetate (47 mg) and triphenylphosphine (105 mg) in one portion. The reaction mixture was then heated to 55° C. and held at that temperature. After the reaction temperature reached 55° C., a second portion of 47% K$_2$CO$_3$ (3.56 g) and a third portion were added via syringe after 1 hr and 2 hr, respectively. The reaction was stopped after 9 hr, with an in-process yield of 91.8% of methyl 4-amino-3-chloro-6-(4-chloro-2-fluoro-3-methoxyphenyl)pyridine-2-carboxylate.

A crude AP-Me feed (41.4 g, which corresponds to 8.8 g, 40.0 mmol of AP-Me) was distilled to remove ~⅔ of methanol until the residual weight reached 21.2 g. A thick slurry was retained and redissolved with 13.1 g of MeCN (8 eq.) and 23.1 g MIBK. ABA (9.4 g, 1.15 eq) and water (40.4 g) were added to the AP-Me solution. 3.2 g 47 wt % K$_2$CO$_3$ solution was added, and the resulting mixture was sparged with nitrogen for 30 min. After sparging, 3.56 g 47% K$_2$CO$_3$ was added to the mixture, followed by palladium acetate (47 mg) and triphenylphosphine (105 mg) in one portion. The reaction mixture was then heated to 55° C. and held at that temperature. After the reaction temperature reached 55° C., a second portion of 47% K$_2$CO$_3$ (3.56 g) and a third portion were added via syringe after 1 hr and 2 hr, respectively. The reaction was monitored by LC after the reaction reached 55° C. The reaction was stopped after 24 hr, with an in-process yield of 70.4% of methyl 4-amino-3-chloro-6-(4-chloro-2-fluoro-3-methoxyphenyl)pyridine-2-carboxylate.

A crude AP-Me feed (41.4 g, which corresponds to 8.8 g, 40.0 mmol of AP-Me) was distilled to remove ~⅔ of methanol until the residual weight reached 20 g. A thick slurry was retained and redissolved with 26.2 g MeCN (16 eq.). ABA (9.4 g, 1.15 eq) and water (40.4 g) were added to the AP-Me solution. 3.2 g 47 wt % K$_2$CO$_3$ solution was added, and the resulting mixture was sparged with nitrogen for 30 min. After sparging, 3.56 g 47% K$_2$CO$_3$ was added to the mixture, followed by palladium acetate (47 mg) and triphenylphosphine (105 mg) in one portion. The reaction mixture was then heated to 55° C. and held at that temperature. After the reaction temperature reached 55° C., a second portion of 47% K$_2$CO$_3$ (3.56 g) and a third portion were added via syringe after 1 hr and 2 hr, respectively. The reaction was monitored by LC. The reaction was stopped after 24 hr, with an in-process yield of 77.2% of methyl 4-amino-3-chloro-6-(4-chloro-2-fluoro-3-methoxyphenyl)pyridine-2-carboxylate.

A crude AP-Me feed (41.4 g, which corresponds to 8.8 g, 40.0 mmol of AP-Me) was distilled to remove ~⅔ of methanol until the residual weight reached 21.5 g. A thick slurry was retained and redissolved with 36.2 g MIBK, ABA (9.4 g, 1.15 eq), and water (40.4 g). 3.2 g 47 wt % K$_2$CO$_3$ solution was added, and the resulting mixture was sparged with nitrogen for 30 min. After sparging, 3.56 g 47% K$_2$CO$_3$ was added to the mixture, followed by palladium acetate (47 mg) and triphenylphosphine (105 mg) in one portion. The reaction mixture was then heated to 55° C. and held at that temperature. After the reaction temperature reached 55° C., a second portion of 47% K$_2$CO$_3$ (3.56 g) and a third portion were added via syringe after 1 hr and 2 hr, respectively. The reaction was monitored by LC after the reaction reached 55° C. The reaction was stopped after 24 hr, with an in-process yield of 78.1% of methyl 4-amino-3-chloro-6-(4-chloro-2-fluoro-3-methoxyphenyl)pyridine-2-carboxylate.

In a round bottom flask, 174.0 g of crude methyl 4-amino-3,6-dichloropyridine-2-carboxylate (AP-Me) solution (which corresponds to 38.5 g, 174.0 mmol of AP-Me) was distilled under reduced pressure to a slurry. 4-methyl-2-pentanone (MIBK) (~120 g) was added and the solution was again distilled under reduced pressure to a slurry. Additional MIBK (~120 g) was added and the solution was distilled a final time under reduced pressure to a slurry. Acetonitrile (112.0 g, 2728 mmol) was added and ¹HNMR analysis of the mixture indicated no presence of methanol. The mixture was transferred to a jacketed 1 L reactor with an additional acetonitrile rinse (35.1 g, 855 mmol). Water (189 g) and K$_2$CO$_3$ solution (47 wt %, 11.9 g, 40.5 mmol) were added to achieve a neutral pH, then 4-chloro-2-fluoro-3-methoxyphenylboronic acid (ABA) (39.6 g, 91.4 mmol) was added. The mixture was sparged with nitrogen for 45 minutes before adding additional 47 wt % K$_2$CO$_3$ solution (16.0 g, 54.4 mmol), triphenylphosphine (0.46 g, 1.8 mmol) and palladium acetate (0.20 g, 0.9 mmol). The reaction was heated to 60° C. Additional 47 wt % K$_2$CO$_3$ solution was added at 30 minutes (16.0 g, 54.4 mmol), 60 minutes (12.2 g, 41.5 mmol), and 90 minutes (9.0 g, 30.6 mmol) after reaching 60° C. After 19 hr, the reaction was heated to 65° C. and then phase separated. The organic phase was analyzed to afford 85.0% yield of methyl 4-amino-3-chloro-6-(4-chloro-2-fluoro-3-methoxyphenyl)pyridine-2-carboxylate.

Crude AP-Me solution (22.5 wt %, 28 g, which corresponds to 6.3 g, 28.5 mmol of AP-Me) was added to a round bottom flask. ABA (6.7 g), methanol (10 g), and triethylamine (11.5 g) were added. The mixture was sparged with nitrogen for 25 min and then palladium acetate (64 mg) and triphenylphosphine (150 mg) were added. The mixture was heated to 50° C. and sampled via GC after 18 hr, with the conversion being 81%. The mixture was further heated to 65° C. and the conversion was 85% after 6 hr at 65° C.

Crude AP-Me solution (22.5 wt %, 20 g, which contained 4.5 g, 20.4 mmol of AP-Me) was added to a round bottom flask. ABA (4.8 g), methanol (10 g), and diisopropylamine (8.94 g) were added. The mixture was sparged with nitrogen for 15 min and then palladium acetate (46 mg) and triphenylphosphine (107 mg) were added. The mixture was heated to 50° C. The reaction conversion was 84% after 22 hr.

Example 6. Workup Prior to Direct Coupling 4-amino-3,6-dichloropyridine-2-carboxylic acid (AP) (40.0 g, 193.2 mmol) then methanol (129.3 g, 4035 mmol) were added to a jacketed reactor. Using an addition funnel, concentrated sulfuric acid (7.1 g, 72.1 mmol) was added dropwise. The resulting slurry was heated to reflux (~65° C.) and allowed to react for 16 hours at which time the resulting clear solution was cooled to room temperature. 4-methyl-2-pentanone (MIBK) (206.6 g, 2063 mmol) was added to the crude reaction mixture followed by a 12 wt % solution of potassium bicarbonate (79.6 g, 95.4 mmol) resulting in a pH-8.0. After stirring for 15 minutes, a saturated aqueous solution of sodium chloride (59.4 g) was added and stirred for an additional 15 minutes before phase separating. The organic solution containing methyl 4-amino-3,6-dichloro-pyridine-2-carboxylate (AP-Me) was added back to the jacketed reactor and distilled under reduced pressure to a concentration of 35.5 wt % AP-Me. The resulting slurry was cooled to ambient temperature at which time 4-chloro-2-fluoro-3-methoxy-phenylboronic acid (ABA) (38.42 g, 188.5 mmol), methanol (17.3 g, 539.6 mmol), and acetonitrile (110.5 g, 2693 mmol) were added. In a flask was added water (168.5 g) and potassium bicarbonate (42.1 g, 420.7 mmol). Both the reactor contents and aqueous base flask were sparged with nitrogen gas for 45 minutes at which time the aqueous base solution was added to the reactor. Triphenylphosphine (0.441 g, 1.683 mmol) and palladium acetate (0.189 g, 0.841 mmol) were added in one portion and the reactor contents were heated at 50° C. for 23 hours. The reactor temperature was increased to 65° C. then the contents were drained into a hot separatory funnel and phase separated to afford 84.2% in process yield of methyl 4-amino-3-chloro-6-(4-chloro-2-fluoro-3-methoxyphenyl)pyridine-2-carboxylate.

A crude AP-Me feed (which contained 8.8 g, 40 mmol of AP-Me) was diluted with 41.4 g of MIBK. MeOH, water, and MIBK were removed via rotavapor until the residual weight reached 21.5 g. An oily mixture was left in the flask, which contained around 10 g MIBK. MeCN (26.2 g, 16 eq.) was added, followed by ABA solid (9.4 g, 1.15 eq.), MeOH (4.3 g), and water (41.6 g). 3.37 g 47 wt % $K_2CO_3$ solution was added, and the resulting mixture was sparged with nitrogen for 30 min. After sparging, 3.56 g 47% $K_2CO_3$ was added to the mixture, followed by palladium acetate (47 mg) and triphenylphosphine (105 mg). The reaction mixture was then heated to 55° C. and held at that temperature. After the reaction temperature reached 55° C., a second portion of 47% $K_2CO_3$ (3.56 g) and a third portion were added via syringe after 1 hr and 2 hr, respectively. The reaction was stopped after 16 hr, with an in process yield of 92.6% of methyl 4-amino-3-chloro-6-(4-chloro-2-fluoro-3-methoxy-phenyl)pyridine-2-carboxylate.

A crude AP-Me feed (which contained 8.8 g, 40.0 mmol of AP-Me) was charged to a rotavapor to remove ~⅔ of methanol until the residual weight reached 20.5 g. A thick slurry was retained and redissolved with 26.2 g MeCN (16 eq.). ABA (9.4 g, 1.15 eq.), MIBK (9.8 g), MeOH (4.3 g), and water (40.4 g) were added to the AP-Me solution. 3.37 g of 47 wt % $K_2CO_3$ solution was added, and the resulting mixture was sparged with nitrogen for 30 min. After sparging, 3.56 g 47% $K_2CO_3$ was added to the mixture, followed by palladium acetate (47 mg) and triphenylphosphine (105 mg). The reaction mixture was then heated to 55° C. and held at that temperature. After the reaction temperature reached 55° C., a second portion of 47% $K_2CO_3$ (3.56 g) and a third portion were added via syringe after 1 hr and 2 hr, respectively. The reaction was stopped after 9 hr, with an in process yield of 91.8% methyl 4-amino-3-chloro-6-(4-chloro-2-fluoro-3-methoxyphenyl)pyridine-2-carboxylate.

A crude AP-Me feed (189.2 g, which contained 40.0 g, 181.0 mmol of AP-Me)) was distilled via rotavapor to remove ~⅔ of methanol until the residual weight reached 86.8 g. A thick slurry was retained and 11.3 g MeOH was loaded to attain the desired MeOH level. MeCN (118.7 g, 16 eq.), ABA solid (42.5 g, 1.15 eq.), MeOH (19.1 g), MIBK (44.7 g), and water (182.9 g) were added to the mixture. 14.5 g 47 wt % $K_2CO_3$ solution was added, and the resulting mixture was sparged with nitrogen for 45 min. After sparging, 16.1 g 47% $K_2CO_3$ was added to the mixture, followed by palladium acetate (203 mg) and triphenylphosphine (474 mg) in one portion. The reaction mixture was then heated to 55° C. and held at that temperature. After the reaction temperature reached 55° C., a second portion of 47% $K_2CO_3$ (16.1 g) and a third portion were added via syringe after 1 hr and 2 hr, respectively. The reaction was stopped after 10 hr, with an in process yield of 89.1%.

We claim:

1. A method for preparing 6-aryl-4-aminopicolinates of the formula:

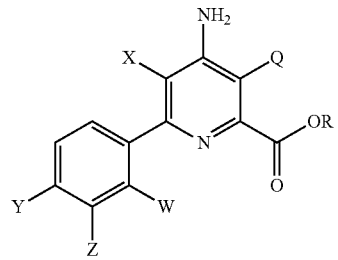

wherein
Q represents hydrogen or halogen;
R represents hydrogen, alkyl, aryl, or arylalkyl;
W represents H, halogen, $C_{1-4}$ alkyl or $C_{1-3}$ alkoxy;
X represents H;
Y represents halogen, $C_{1-4}$ alkyl, or $C_{1-3}$ alkoxy; and
Z represents H, halogen, $C_{1-4}$ alkyl, or $C_{1-3}$ alkoxy
the method comprising coupling an aminopyridine (AP) and a phenyl boronic acid (PBA) by direct Suzuki coupling in the presence of a catalyst, wherein the concentration of the catalyst is less than or equal to about 3% relative to the limiting reagent and the yield of the 6-aryl-4-aminopicolinate is at least about 60%.

2. A method for preparing 6-aryl-4-aminopicolinates of the formula:

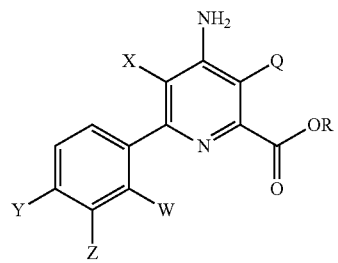

wherein
- Q represents hydrogen or halogen;
- R represents hydrogen, alkyl, aryl, or arylalkyl;
- W represents H, halogen, $C_{1-4}$ alkyl, or $C_{1-3}$ alkoxy;
- X represents F, Cl, $C_{1-4}$ alkyl, $C_{1-3}$ alkoxy, or $-NO_2$;
- Y represents halogen, $C_{1-4}$ alkyl, or $C_{1-3}$ alkoxy; and
- Z represents H, halogen, $C_{1-4}$ alkyl, or $C_{1-3}$ alkoxy the method comprising coupling an aminopyridine (AP) and a phenyl boronic acid (PBA) by direct Suzuki coupling in the presence of a catalyst, wherein the concentration of the catalyst is less than or equal to about 3% relative to the limiting reagent and the yield of the 6-aryl-4-aminopicolinate is at least about 60%.

3. The method of claim 1, wherein the AP is methyl 4-amino-3,6-dichloropyridine-2-carboxylate (AP-Me).

4. The method of claim 2, wherein the AP is benzyl 4-amino-3,6-dichloropyridine-5-fluoro-2-carboxylate (AP-Bz).

5. The method of claim 1, wherein the AP is crude.

6. The method of claim 3, wherein the AP is crude.

7. The method of claim 2, wherein the AP is crude.

8. The method of claim 4, wherein the AP is crude.

9. The method of claim 6, wherein the PBA is 4-chloro-2-fluoro-3-methoxy-phenylboronic acid.

10. The method of claim 6, wherein the PBA is dimethyl (4-chloro-2-fluoro-3-methoxyphenyl)boronate.

11. The method claim 1, wherein the catalyst is a palladium catalyst.

12. The method of claim 11, wherein the palladium catalyst is a palladium (II) catalyst.

13. The method of claim 12, wherein the palladium (II) catalyst is palladium acetate, $Pd(OAc)_2$.

14. The method of claim 6, wherein the PBA is dimethyl (4-chloro-2-fluoro-3-methoxyphenyl)boronate.

15. The method claim 2, wherein the catalyst is a palladium catalyst.

16. The method of claim 15, wherein the palladium catalyst is a palladium (II) catalyst.

17. The method of claim 16, wherein the palladium (II) catalyst is palladium acetate, $Pd(OAc)_2$.

18. The method of claim 1, wherein the concentration of the catalyst is from about 0.2% to about 2.0% relative to the limiting reagent.

19. The method of claim 18, wherein the concentration of the catalyst is from about 0.4% to about 1.0%.

20. The method of claim 19, wherein the concentration of the catalyst is about 0.5%.

21. The method of claim 2, wherein the concentration of the catalyst is from about 0.2% to about 2.0% relative to the limiting reagent.

22. The method of claim 21, wherein the concentration of the catalyst is from about 0.4% to about 1.0%.

23. The method of claim 22, wherein the concentration of the catalyst is about 0.5%.

24. The method of claim 1, wherein the pH of the Suzuki coupling reaction is from about 7 to about 12.

25. The method of claim 24, wherein the pH of the Suzuki coupling reaction is from about 7 to about 10.

26. The method of claim 25, wherein the pH of the Suzuki coupling reaction is from about 8 to about 10.

27. The method of claim 24, wherein the pH is adjusted by the addition of a base and/or $CO_2$.

28. The method of claim 27, wherein the base comprises $K_2CO_3$.

29. The method of claim 27, wherein the base is added in more than one portion during the direct Suzuki coupling.

30. The method of claim 29, wherein the portions are added over a period of at least two hours.

31. The method of claim 2, wherein the pH of the Suzuki coupling reaction is from about 7 to about 12.

32. The method of claim 27, wherein the pH of the Suzuki coupling reaction is from about 7 to about 10.

33. The method of claim 28, wherein the pH of the Suzuki coupling reaction is from about 8 to about 10.

34. The method of claim 28, wherein the pH is adjusted by the addition of a base and/or $CO_2$.

35. The method of claim 34, wherein the base comprises $K_2CO_3$.

36. The method of claim 35, wherein the base is added in more than one portion during the direct Suzuki coupling.

37. The method of claim 36, wherein the portions are added over a period of at least two hours.

38. The method of claim 1, wherein the direct Suzuki coupling is performed in a solvent system comprising a mixture of methyl isobutyl ketone, acetonitrile, and methanol.

39. The method of claim 2, wherein the direct Suzuki coupling is performed in a solvent system comprising a mixture of methyl isobutyl ketone, acetonitrile, and methanol.

40. The method of claim 1, wherein the direct Suzuki coupling was performed in a non-aqueous system.

41. The method of claim 2, wherein the direct Suzuki coupling was performed in a non-aqueous system.

42. The method of claim 1 wherein the compound, 6-aryl-4-aminopicolinate, is produced.

43. The method of claim 42 wherein the yield of said compound is greater than about 60%, 70%, 75%, 80%, 81%, 82%, 83%, 84%, 85%, 86%, 87%, 88%, 89%, 90%, 91%, 92%, 93%, 94%, or 95%.

44. The method of claim 2 wherein the compound, 6-aryl-4-aminopicolinate, is produced.

45. The method of claim 44 wherein the yield of said compound is greater than about 60%, 70%, 75%, 80%, 81%, 82%, 83%, 84%, 85%, 86%, 87%, 88%, 89%, 90%, 91%, 92%, 93%, 94%, or 95%.

* * * * *